United States Patent [19]

Fitzpatrick

[11] 4,303,671

[45] Dec. 1, 1981

[54] ALBUMIN STABILIZED PROSTACYCLIN

[75] Inventor: Francis A. Fitzpatrick, Kalamazoo, Mich.

[73] Assignee: The Upjohn Company, Kalamazoo, Mich.

[21] Appl. No.: 168,846

[22] Filed: Jul. 10, 1980

[51] Int. Cl.$^3$ ............................................. A61K 31/34
[52] U.S. Cl. ................................... 424/285; 424/305; 424/317
[58] Field of Search ...................... 424/305, 317, 285

[56] References Cited

FOREIGN PATENT DOCUMENTS 7245 1/1980 European Pat. Off. .
2819447 11/1978 Fed. Rep. of Germany .

OTHER PUBLICATIONS

Gueriguian-Chem. Abst. vol. 85 (1976), p. 15664y.
A. K. Pedersen, The Lancet, 29 Jul. 1978 (p. 270).
K. Jorgensen, et al., The Lancet i, 1352 (1979).
O. Miller, et al., J. Pharmacol. Exp. Ther., 210:134–140 (1979).
M. Steer, et al., Nature 283:194–195 (1980).
Borda, et al., "Human Platelet Rich Plasma and Human Serum Protects from Inactivation the Antiaggregatory Effect of Prostacyclin . . . " Prostaglandins 19:899–905 (1980).
Johnson, R.A., Prostaglandins 12:915–928.
Bunting, S., et al., Prostaglandins 12:897–913 (1976).
Norman, P.S., et al., "Human Serum Albumin in Tween 80 as Stabilizers of Allergen Solutions", J. Allergy Clin. Immunol. 62:314–319 (1978).
Stanaszek, W. F., et al., "Anesthetic Gas Absorption Properties of Surfactant Systems", J. Pharm. Sci. 61:860–862 (1972).
J. B. McClenahan, et al., "Protein Components of Human Sufactant", Clinical Research 16:134 (1968).
G. Folco, et al., "Albumin Stabilizes Thromboxane A$_2$", FEBA Letters 82:321–324.
D. D. Pifer, et al., "Stabilization of PGI$_2$ by Human Plasma and Human Serum Albumin", published abstract from an FASEB Meeting in Anaheim, California (Apr. 14–20, 1980).
Rao, et al., "Influence of pH on Prostacyclin Mediated Inhibition of Platelet Function", Prostaglandins and Medicine 4:263–273 (1980).
M. J. Cho, et al., "Chemical Stability of Prostacyclin (PGI$_2$) in Aqueous Solutions", Prostaglandins 15:943–954 (1978).
M. Wynelda, et al., "High Performance Liquid Chromatographic Assay for Prostacyclin", J. Chromatogr. 176:413–417 (1979).

*Primary Examiner*—Sam Rosen
*Attorney, Agent, or Firm*—L. Ruth Hattan; Robert A. Armitage

[57] ABSTRACT

The present invention provides novel formulations of prostacyclin suitable for parenteral administration and methods for making and using these formulations. These novel formulations include a pharmaceutically acceptable stabilizing concentration of albumin as a constituent thereof. Such novel formulations of prostacyclin are useful for its conventional pharmacological and therapeutical purposes, most to inhibition of blood platelet aggregation.

4 Claims, No Drawings

ALBUMIN STABILIZED PROSTACYCLIN

DESCRIPTION

1. Background of the Invention

The present invention relates to novel compositions and methods of using prostacyclin for human and veterinary pharmaceutical purposes. Particularly, the present invention relates to novel stabilized compositions of prostacyclin, and methods of preparing and using these stabilized solutions. Most particularly, the present invention relates to stabilized compositions of prostacyclin and methods for preparing them and using them in formulations suitable for parenteral administration in mammals.

Prostacyclin is a carboxylic acid derived biosynthetically from arachidonic acid and exhibits the chemical structure and carbon atom numbering of formula I. Prostacyclin can be trivially named as 9-deoxy-6,9$\alpha$-epoxy-(5Z)-5,6-didehydro-PGF$_1$. For a description of prostacyclin and its structural identification, see Johnson, R. A., Prostaglandins 12:915–928 (1976). For a description of the biosynthesis and cardiovascular pharmacology of prostacyclin, see Bunting, S., et al., Prostaglandins 12:897–913 (1976).

At the time of its discovery, prostacyclin represented the most potent prostaglandin-related substance effective to inhibit blood platelet aggregation. Because of this profound pharmacological action, as well as other pharmacological actions of prostacyclin, prostacyclin has been employed for a wide variety of pharmacological, veterinary, and clinical purposes. Prostacyclin is most efficaciously employed using parenteral routes of administration, typically intravenous or intra-arterial administration.

Under acid conditions, including at physiological pH's, prostacyclin spontaneously decomposes to 6-oxo-PGF$_{1\alpha}$, a compound of formula II. Accordingly, in parenteral formulations of prostacyclin, its relative chemical instability presents a significant problem.

One means of stabilizing pharmaceutical formulations of prostacyclin is by preparing formulations at high pH (e.g., pH 10). However, use of such non-physiologic pH solutions is neither pharmaceutically elegant nor free from adverse effects on the patient or animal to whom the solution is being administered.

Other means of stabilizing solutions of prostacyclin-type compounds are described in German Offenlegungsschrift No. 2,819,447 (abstracted and published as Derwent Farmdoc CPI No. 82551A), consisting of solutions of the prostacyclin-type compound in pharmacologically acceptable alcohols, polar aprotic solvents, or triglycerides of specified chain lengths. German Offenlegungsschrift No. 2,819,447 also describes cyclodextrin clathrates of PGI$_2$ compounds as stabilized compositions.

Yet another method of stabilizing pharmaceutical compositions of prostacyclin is through employment of pharmaceutical diluents containing surfactants. See European published Patent application No. 7,245, reported in the European Patent Bulletin of 23 January 1980 and abstracted and published under Derwent Farmdoc CPI No. 05863C.

The present invention provides for stabilization of PGI$_2$ formulations suitable for parenteral administration by employing serum albumin as an excipient in such formulations. Albumins are proteins found in nearly every animal and in many vegetable tissues and are characterized by being soluble in water and coagulable by heat. Albumins contain carbon, hydrogen, nitrogen, oxygen, and sulphur. Serum albumin is the chief protein component of blood plasma and is used, for example, intravenously in the treatment of shock.

Other uses of human serum albumin include use as stabilizers of allergenic solutions. See Norman, P. S., et al., "Human Serum Albumin in Tween 80 as Stabilizers of Allergen Solutions", J. Allergy Clin. Immunol. 62:314–319 (1978). Also, Stanaszek, W. F., et al., "Anesthetic Gas Absorption Properties of Surfactant Systems", J. Pharm. Sci. 61:860–862 (1972) report that surfactant concentration is an important factor in anesthetic gas absorption, employing bovine albumin as one surfactant system. J. B. McClenahan, et al., "Protein Components of Human Surfactant", Clinical Research 16:134 (1968) report studies undertaken to determine the protein component of the primary lipid of the human surfactant lipoprotein molecule and report that albumin is closely associated with the surfactant molecule and may constitute the protein component.

A further use of albumin is its reported ability to stabilize thromboxane A$_2$, an arachidonic acid metabolite of formula III. See G. Folco, et al., "Albumin Stabilizes Thromboxane A$_2$", FEBS Letters 82:321–324 (1977).

A. K. Pedersen, The Lancet, July 29, 1978 (page 270), reports that prostacyclin is probably protected against degradation when kept in whole blood or plasma. Further confirmation of this finding is provided by K. Jorgensen, et al., The Lancet i, 1352 (1979), O. Miller, et al., J. Pharmacol. Exp. Ther., 210:134–140 (1979), and M. Steer, et al., Nature 238:194–195 (1980). See also Borda, et al., "Human Platelet Rich Plasma and Human Serum Protects from Inactivation the Antiaggregatory Effect of Prostacyclin . . . ", Prostaglandins 19:899–905 (1980).

Finally, subsequent to any invention described herein D. D. Pifer, et al., "Stabilization of PGI$_2$ by Human Plasma and Human Serum Albumin", published abstract from an FASEB Meeting in Anaheim, California (Apr. 14–20, 1980), indicate that albumin stabilizes prostacyclin. See also Rao, et al., "Influence of pH on Prostacyclin Mediated Inhibition of Platelet Function", Prostaglandins in Medicine 4:263–273 (1980), reporting effects of pH in albumin on prostacyclin-mediated inhibition of platelet function.

Finally, for a general discussion of the methodology and results of stability determinations for prostacyclin in aqueous solutions, see M. J. Cho, et al., "Chemical Stability of Prostacyclin (PGI$_2$) in Aqueous Solutions", Prostaglandins 15:943–954 (1978), and M. Wynelda, et al., "High Performance Liquid Chromatographic Assay for Prostacyclin", J. Chromatogr. 176:413–417 (1979).

3. Prior Art

The protective effect of whole blood or plasma against degradation of prostacyclin is known in the art. Other methods of stabilization of parenteral formulations of prostacyclin are also known in the art, and include the use of alcohols, polar aprotic solvents, triglycerides, and surfactants.

SUMMARY OF THE INVENTION

The present invention particularly provides (a) In a method consisting essentially of administering prostacyclin to a mammal in a formulation suitable for parenteral administration, the improvement which comprises:

employing as an excipient in said formulation in a pharmaceutically acceptable, stabilizing concentration albumin derived from serum obtained from the species of which said mammal is a member.

(b) In a composition consisting essentially of a formulation of prostacyclin suitable for parenteral administration, the improvement which comprises:

albumin derived from serum obtained from the species of which said mammal is a member, employed as an excipient in said formulation in a pharmaceutically acceptable, stabilizing concentration.

(c) A method of stabilizing prostacyclin in a formulation suitable for parenteral administration to a mammal, which comprises (1) preparing a conventional pharmaceutical diluent for said formulation, (2) adding to said conventional diluent a pharmaceutically acceptable, stabilizing concentration of albumin derived from serum obtained from the species of which said mammal is a member, thereby preparing a stabilizing diluent, and (3) combining with a quantity of said stabilizing diluent an amount of a pharmacologically acceptable salt of prostacyclin whereby a predetermined, pharmaceutically-acceptable concentration of prostacyclin is obtained in the resulting solution, (d) A formulation of prostacyclin suitable for parenteral administration to a mammal, which comprises:

(1) a quantity of a conventional pharmaceutical diluent for said formulation, (2) an amount of albumin derived from serum obtained from the species of which said mammal is a member, which when combined with said quantity of conventional diluent yields a stabilizing diluent wherein said albumin is present in a pharmaceutically acceptable, stabilizing concentration; and (3) an amount of a pharmacologically acceptable salt of prostacyclin, which when combined with said stabilizing diluent yields a predetermined, pharmaceutically-acceptable concentration of prostacyclin in the resulting solution.

The compositions prepared in accordance with the present invention all exhibit surprisingly and unexpectedly improved stability, permitting greater ease of handling, more efficacious pharmacological or therapeutical effects, and greater versatility in preparing suitable parenteral formulations. With regard to the latter consideration, the compositions in accordance with the present claims are surprisingly more stable even when such formulations are prepared at physiological pH levels. Moreover, these formulations avoid the use of other non-physiologic stabilizing techniques of the prior art, e.g., detergent-like chemical surfactants, polar aprotic solvents and alcohols.

In accordance with the invention as summarized above, prostacyclin refers to the chemical compound of formula I, including the various salt forms thereof.

Mammals to whom the novel compositions of prostacyclin are administered include all valuable domestic and experimental mammalians, but most especially and preferredly humans.

Formulations of prostacyclin suitable for parenteral administration are known in the art. As indicated above, parenteral administration includes especially intravenous and intraarterial administration, although other parenteral routes are also contemplated by the present invention, e.g., intramuscular and intraperitoneal. Such conventional formulations are typically aqueous solutions of a salt of prostacyclin, containing buffers as excipients in order to elevate pH. Additionally, such formulations contain optionally other excipients, such as preservatives and sodium chloride. Such vehicles (the aqueous solution containing the excipients) comprise the conventional pharmaceutical diluents employed in accordance with the compositions and methods of the present claims.

The albumin used in accordance with a formulation of the present invention is derived from the serum of an animal from the species to which the formulation is to be administered. For example, human serum albumin is employed in formulations of the present invention intended for administration to humans. Thus, the possibility of allergenic reactions to the formulation is minimized.

Albumin employed in accordance with the present invention is most preferably serum albumin, obtained by conventional and known techniques. For example, human serum albumin is readily available and is, in fact, employed therapeutically, as indicated above.

Albumin is employed in the compositions in accordance with the present invention in a pharmaceutically acceptable, stabilizing concentration. Pharmaceutically acceptable concentrations include all concentration levels wherein the presence of the albumin is not sufficient to manifest any toxic effects. Since albumin is a relatively non-toxic protein, a wide range of concentrations of albumin, including relatively high concentrations, may be safely employed in accordance with the present invention.

Stabilizing concentrations of albumin refer to concentrations wherein the stabilizing effects of the albumin on the solution is manifest. Accordingly, the requirement that the albumin be present in the formulation is a requirement that the concentration thereof equal or exceed the minimum concentration wherein the stabilizing effect is observed. While the minimum concentration of albumin necessary to stabilize the formulation will depend upon the pH of the prostacyclin formulation, ordinarily at least 50–500 parts by weight of albumin are required to stabilized one part by weight of prostacyclin. Accordingly, the pharmaceutically acceptable, stabilizing concentration of albumin in accordance with the present invention will range from about 50 parts by weight of albumin per part by weight of prostacyclin to about 5000 parts by weight per part by weight of prostacyclin.

The presence of a pharmaceutically acceptable stabilizing concentration of albumin in a conventional pharmaceutical diluent for prostacyclin yields the stabilizing diluent in accordance with the present invention. Into this stabilizing diluent is combined a salt of prostacyclin (e.g., sodium salt or another pharmacologically acceptable salt) to form the finished formulation suitable for parenteral administration. Accordingly, there is obtained for use a stabilized formulation of prostacyclin preferably within the physiological pH range of 7.2–7.6 (optionally within a pH range of 4–12), suitable for use in administration to a mammal derived.

DESCRIPTION OF THE PREFERRED EMBODIMENTS

The present invention is further described by the following example:

EXAMPLE 1

Prostacyclin sodium salt, as a free flowing solid, (1 part by weight) and human serum albumin (either 200 or 500 parts by weight) are dissolved by adding a 0.1 M phosphate buffer, pH 7.4, and 0.9% sodium chloride. A similar solution containing prostacyclin and buffer, but no albumin, is also prepared.

The relative stabilities of these three formulations are as follows:

| Number | Albumin | Half-life | % Residual |
|--------|---------|-----------|------------|
| 1 | 500 | 57.6 | >30 |
| 2 | 200 | 30.2 | >10 |
| 3 | 0 | 20.9 | ~5 |

Half-life is expressed in minutes and % Residual is the percentage of prostacyclin remaining in solution after 100 minutes. All solutions were stored at 4° C. during the course of the experiment.

FORMULAS

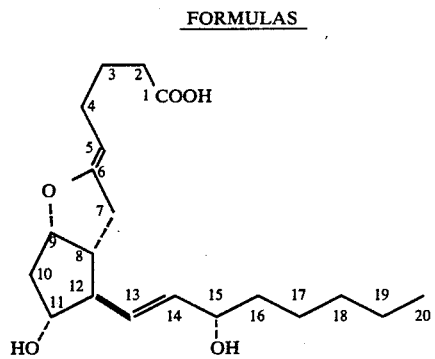

I

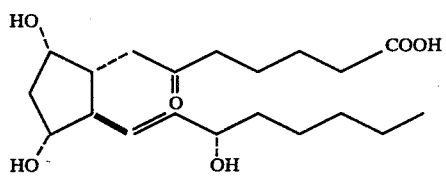

II

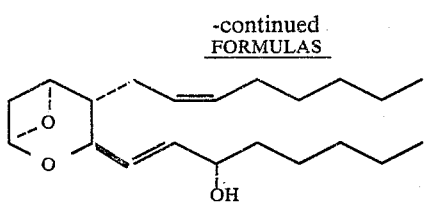

III

I claim:

1. In a method consisting essentially of administering prostacyclin to a mammal in a formulation suitable for parenteral administration, the improvement which comprises:
    employing as an excipient in said formulation in a pharmaceutically acceptable, stabilizing concentration albumin derived from serum obtained from the species of which said mammal is a member.

2. In a composition consisting essentially of a formulation of prostacyclin suitable for parenteral administration, the improvement which comprises:
    albumin derived from serum obtained from the species of which said mammal is a member, employed as an excipient in said formulation in a pharmaceutically acceptable, stabilizing concentration.

3. A method of stabilizing prostacyclin in a formulation suitable for parenteral administration to a mammal, which comprises
    (1) preparing a conventional pharmaceutical diluent for said formulation,
    (2) adding to said conventional diluent a pharmaceutically acceptable, stabilizing concentration of albumin derived from serum obtained from the species of which said mammal is a member, thereby preparing a stabilizing diluent, and
    (3) combining with a quantity of said stabilizing diluent an amount of a pharmacologically acceptable salt of prostacyclin whereby a predetermined, pharmaceutically-acceptable concentration of prostacyclin is obtained in the resulting solution.

4. A formulation of prostacyclin suitable for parenteral administration to a mammal, which comprises:
    (1) a quantity of a conventional pharmaceutical diluent for said formulation,
    (2) an amount of albumin derived from serum obtained from the species of which said mammal is a member,
    which when combined with said quantity of conventional diluent yields a stabilizing diluent wherein said albumin is present in a pharmaceutically acceptable, stabilizing concentration; and
    (3) an amount of a pharmacologically acceptable salt of prostacyclin, which when combined with said stabilizing diluent yields a predetermined, pharmaceutically-acceptable concentration of prostacyclin in the resulting solution.

* * * * *